United States Patent [19]

Leuenberger

[11] 4,111,208

[45] Sep. 5, 1978

[54] PROCESS FOR DRILLING HOLES IN HARD MATERIALS, IN SURGICAL PROCEDURES, AND APPARATUS FOR CARRYING OUT THE PROCESS

[76] Inventor: Roland Leuenberger, 15 chemin du Bois de la Chapelle, 1215 Onex, Geneva, Switzerland

[21] Appl. No.: 810,763

[22] Filed: Jun. 28, 1977

[30] Foreign Application Priority Data

Dec. 22, 1976 [CH] Switzerland .................. 16177/76

[51] Int. Cl.² ............ A61B 17/32; A61B 17/16; B23B 35/00; B23B 39/10
[52] U.S. Cl. ................ 128/305.1; 128/310; 408/1 BD; 408/124
[58] Field of Search ............ 408/1, 124, 125; 128/305, 305.1, 310, 68

[56] References Cited

U.S. PATENT DOCUMENTS

| 1,299,241 | 4/1919 | Sears | 408/124 |
| 2,144,342 | 1/1939 | Morrison | 128/305.1 |
| 2,354,735 | 8/1944 | Bensinger | 408/125 |
| 3,049,018 | 8/1962 | Lusskin et al. | 128/310 |
| 3,682,177 | 8/1972 | Ames et al. | 128/310 |

*Primary Examiner*—Harrison L. Hinson
*Attorney, Agent, or Firm*—Haseltine, Lake & Waters

[57] ABSTRACT

A process and apparatus for drilling holes in hard materials in surgical procedures, comprising driving a drilling tool with a movement of alternating rotation with an amplitude of less than one revolution. The tool can be driven from a motor having unidirectional continuous rotatable movement through a convertor which transforms this movement into the alternating rotation. The drilling tool can covered by a member which feeds the waste cutting materials rearwardly into an enclosed chamber. The apparatus can also be provided with a member that covers the drill during an insertion thereof through cut tissue prior to the drilling operation.

15 Claims, 5 Drawing Figures

PROCESS FOR DRILLING HOLES IN HARD MATERIALS, IN SURGICAL PROCEDURES, AND APPARATUS FOR CARRYING OUT THE PROCESS

FIELD OF THE INVENTION

The present invention relates to a process for drilling holes, in surgical procedures, in hard materials, such as for example, bone and cartilage and it also relates to an apparatus for carrying out the process.

BACKGROUND

The formation of such holes is currently effected by a unidirectional rotatable movement of a boring or drilling tool.

However, such manner of operation requires great precaution in order to avoid damage to soft portions, such as, flesh, muscles, tendons, nerves and vessels. In spite of the precaution taken, injury often occurs such as cutting tendons, nerves, veins or arteries or even winding these around the tool.

SUMMARY OF THE INVENTION

An object of the invention is to provide a method and apparatus by which the above injuries can be avoided without need for great precaution.

The process according to the invention, comprises driving the tool in alternately opposite directions of rotation with an amplitude smaller than one revolution.

The tool can be a drill, a miller, a broaching tool, even a squaring tool.

It is obvious that the considered movement, even if introduced into soft portions, does not exceed the displacements that these can sustain without being damaged.

Furthermore, this alternating movement produces short cuttings which facilitate the removal and the lubrication. It also diminishes heating to a large degree, thus diminishing the risk of modification of the cellular structure, notably bone.

Among other advantages, it is noted that in the case where one utilizes a drill completely traversing the bone, the operator, who often has the task of manually determining the instant where the drill exits, does not risk either damaging the bone or the tissue at the outlet of the drill. The process, in a common concept, facilitates the placement of fixing broches as often, in traumatology, the operator can not take into account the region where such a tool will open.

The process also avoids for the most part, the case for use of a trocar. When one must engage the tool in bone, for example, for mounting a prosthesis, one also does not risk damage of the soft neighboring portions.

The apparatus for carrying out the process comprises a driven member having a support and driving the tool, and means for driving this member with alternating rotation of an amplitude of less than one revolution.

DETAILED DESCRIPTION

Figure 1:
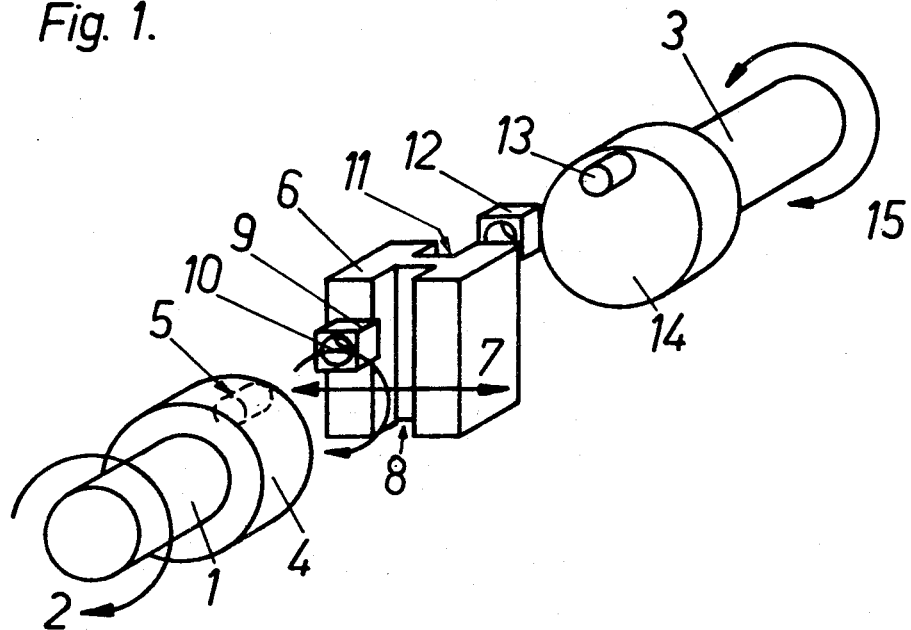
FIG. 1 is a schematic exploded view, in perspective, of a first embodiment according to the invention.

In a first embodiment, a unidirectional rotatable motor (not shown) is at the left with respect to the drawing and communicates a movement of continuous rotation to a shaft 1 in the direction of the arrow 2.

A member, for example, a mandrel adapted to support and drive the drilling tool (not shown) is schematically represented by a cylinder 3 coaxial with the shaft 1.

The mechanism for transformation of the movement from the unidirectional rotation of shaft 1 to an alternating rotation of a magnitude less than one revolution of cylinder 3 is interposed between shaft 1 and cylinder 3.

The shaft 1 drives through the intermediary of a member 4, an eccentric pin 5 secured to member 4 and constituting a crank pin. Facing the crank pin 5 is a block 6 constituting a guided slide which can only be displaced laterally in the direction of the double arrows 7. The slide has a groove 8 facing the crank pin 5, the groove 8 extending perpendicularly to the direction of displacement of the block 6.

A block 9 is slidably mounted in groove 8. The block 9 has a hole 10 which receives the crank pin 5.

When the crank pin 5 is driven with a movement of unidirectional continuous rotation, it causes the block 6 to effect a reciprocal transverse movement in the direction of the arrows 7, the block 9 effecting in turn during this time a reciprocating movement in the groove 8.

Opposed to the groove 8 is a similar groove 11 which is parallel thereto.

This second groove 11 is adapted to reveive a second perforated block 12 similar to block 9. In the hole in the second block 12 is placed a pin 13 constituting a second crank pin fixed to a member 14 secured to the mandrel 3. The moment arm of crank pin 13 is slightly greater than that of the crank pin 5, namely the crank pin 13 is located at a greater radial distance from the axis of rotation of shaft 1 and mandrel 3 as compared to crank pin 5.

The transverse reciprocal movement of the slide 6 will communicate to the member 14 via crank pin 13 a corresponding movement, that is to say, a movement in alternate rotation of an amplitude less than a complete revolution such that the mandrel 3 and with it the tool that it supports will be displaced correspondingly as is indicated by the arrows 15.

If the groove 11 is laterally offset with respect to the groove 8, the result will be the same, but the tool and the motor will no longer be coaxial.

Figure 2:
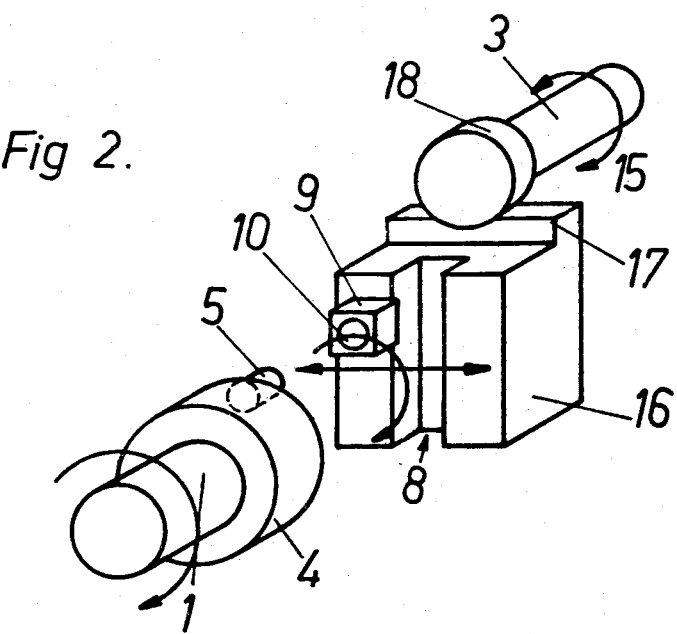
FIG. 2 is a similar view of a second embodiment.

In the second embodiment as shown in FIG. 2, the members 1,4,5,9, and 10 are identical to those which have just been described. A slide block 16 is provided with a groove 8 and it is guided in the same manner as block 6. It differs from block 6 by being provided with a rack 17 extending in the direction of its transverse displacement. The rack will therefore undergo a reciprocating movement in the direction of arrows 7.

The rack 17 meshes with a pinion 18 secured to the member 3 carrying the tool, and the member 3 will execute an alternating rotational movement of an amplitude depending on the diameter of the pinion 18. The latter is selected such that the rotational movement (see arrows 15) remains less than one complete revolution.

Figure 3:
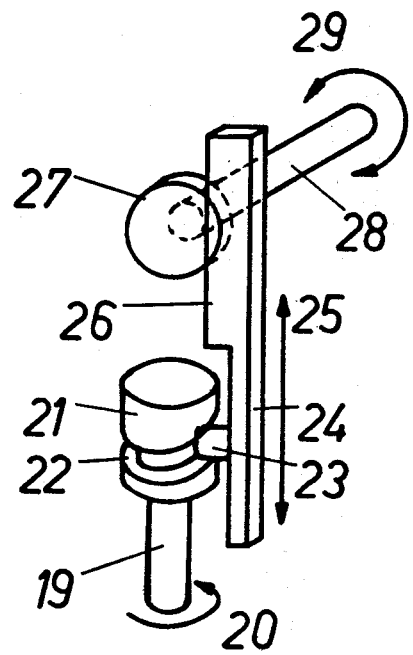
FIG. 3 is a perspective view of a third embodiment.

The third embodiment of FIG. 3, also utilizes a rack and a pinion.

The motor shaft is shown at 19 and turns unidirectionally in the direction of the arrow 20. The shaft 19 supports a head 21 having a circular groove 22 extending in a plane inclined with respect to the axis of rotation of shaft 19 and in which extends a pin 23 secured to a rod 24 which is supported for slidable movement only in the direction of the arrows 25 or parallel to the axis of shaft 19 and head 21.

The rod includes a rack 26 which meshes with a pinion 27 secured to a member 28 carrying the tool.

The unidirectional rotation of the shaft 19 transmits a longitudinal reciprocation movement to the rod 24 and its rack 26 in the direction of arrows 25 and has the effect of communicating to the pinion 27 and to the member 28 a movement of alternating rotation as indicated by the arrows 29.

The desired amplitude of this movement depends on the relative dimensions of the various elements of the assembly.

It follows from this process that in the first embodiment the mandrel is coaxial with the motor member whereas in the second embodiment it is laterally offset, while in the third embodiment it is perpendicular thereto.

This perpendicularity can of course be obtained by other means, such as pinions in combination at an angle, for example, with one of the two first embodiments. One can also provide other directions between 0° and 90° or constructions with a variable angle.

Such angular dispositions are sometimes necessary, but present the difficulty of introduction of the tool through flesh up to the bone.

Figure 4:
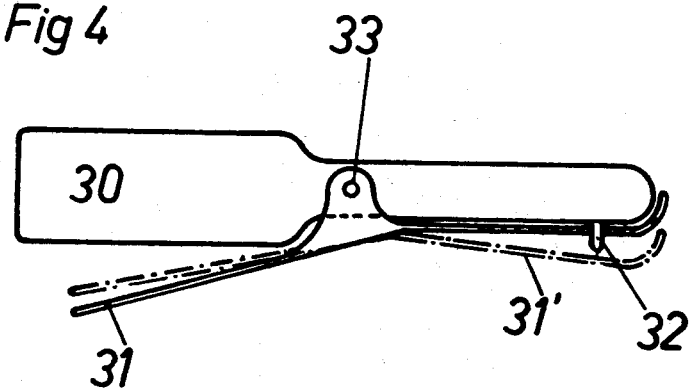
FIG. 4 shows a variant partially in section.

The variation according to FIG. 4 resolves this difficulty. It comprises an elongated apparatus 30 containing all of the elements described heretofore inclusive of the motor and an articulated handle 31 extending the length of the surface of the apparatus 30 from which the tool 32 emerges. The handle 31 is pivotal about a pin 33 in the region of the midlength thereof. The handle 31 has a slot for the passage of the tool 32 which can traverse it and emerge therefrom in the solid line position of 31. In the position shown in chain-dotted lines at 31', the handle covers the tool and permits the introduction of the assembly into the flesh, preliminarily cut, without risk of jamming.

In the particular case where the tool is a helicoidal drill, the latter has the disadvantage of feeding waste coming from the drilling to the rear.

Figure 5:
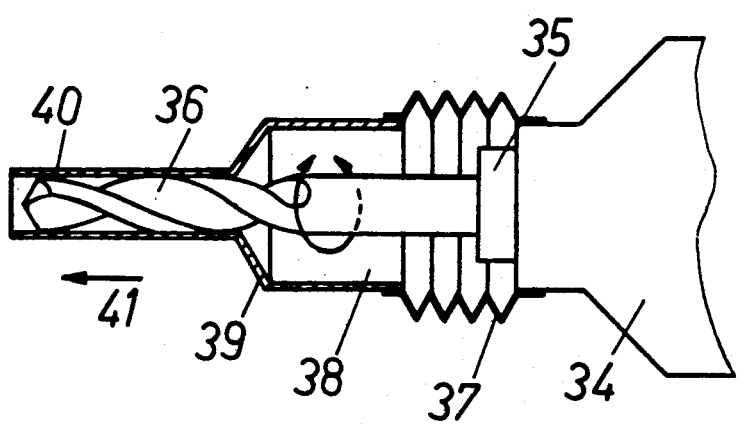
FIG. 5 is a partial sectional view of an accessory for effecting removal of waste.

By completing the apparatus according to the invention by the accessory shown in FIG. 5, this disadvantage is also eliminated.

The apparatus partially shown at 34 includes mandrel 35 carrying a drill 36. At the extremity of the mandrel 35 is an elastic bellows 37 extending in the direction of the drill 36 secured to a cylindrical portion 38 connected to a frustoconical portion 39, in turn connected to a tubular portion 40 surrounding the drill and whose interior diameter corresponds to the exterior diameter of the drill.

The elastic bellows 37 is constituted so as to exert a slight elastic pressure in the direction of the free extremity of the tool 36 in the direction of arrow 41.

In the course of drilling, the tube 40 will be constantly applied against the perforated bone while constituting a channel for evacuation of waste which can accumulate in the rear in the cylindrical portion 38 and in bellows 37.

The amplitude of alternating movement communicated to the tool is preferably greater than the angle of attack of two successive flutes of the drill. A drill having three flutes is particularly shown in order to permit reduction of the angle of rotation below 360° which further reduces the risk previously noted.

The motor can be electrical, hydraulic or pneumatic and can be conceived so as to itself effect an alternating rotational movement.

What is claimed is:

1. A process for drilling holes in hard materials in surgical procedures comprising driving a drilling tool with a movement of alternating rotation with an amplitude of less than one revolution.

2. A process as claimed in claim 1 wherein the drilling tool has at least two offset flutes and the angular movement has an amplitude greater than the offset of two adjacent flutes of the tool.

3. Apparatus for drilling holes in hard materials in surgical procedures comprising a rotatable driving member for attachment to a drilling tool, and means for driving said member in a movement of alternating rotation with an amplitude less than one revolution.

4. Apparatus as claimed in claim 3 wherein said drive means comprises a motor having alternating rotational movement.

5. Apparatus as claimed in claim 3 wherein said drive means comprises a motor having unidirectional continuous rotatable movement, and means interposed between said motor and said driving member for transforming said unidirectional rotational movement into the alternating rotation of an amplitude of less than one revolution.

6. Apparatus as claimed in claim 5 wherein the transforming means comprises a slide member supported for slidable displacement in a transverse direction with respect to the axis of rotation of the motor, a crank pin driven in rotation by said motor, a block slidably mounted in said slide member for movement in a direction perpendicular to the direction of movement of the slide member, a second block slidably mounted in said slide member for movement parallel to the first block, and a second crank pin secured to said driving member and engaged with said second block, said second crank pin being located further from said axis of rotation than the first crank pin.

7. Apparatus as claimed in claim 6 wherein said slide member has opposite faces with parallel grooves therein respectively slidably supporting said blocks.

8. Apparatus as claimed in claim 7 wherein said parallel grooves extend perpendicularly to said axis of rotation.

9. Apparatus as claimed in claim 5 wherein the transforming means comprises a slide member supported for slidable displacement in a transverse direction with respect to the axis of rotation of the motor, a crank pin driven in rotation by said motor, a block slidably mounted in said slide member for movement in a direction perpendicular to the direction of movement of the slide member, a rack on said slide member extending parallel to the direction of movement of the slide member and a pinion secured to said driving member and in mesh with said rack for undergoing rotation in alternately opposite directions during reciprocation of said rack.

10. Apparatus as claimed in claim 5 wherein the transforming means comprises a head driven in rotation by said motor, said head having an annular groove disposed in a plane inclined with respect to said axis of rotation of the motor, a crank pin engaged in said groove, a rod supported for slidable displacement parallel to said axis of rotation, said crank pin being secured to said rod, a rack on said rod, and a pinion secured to said driving member and in mesh with said rack for undergoing rotation in alternately opposite directions during reciprocation of said rack.

11. Apparatus as claimed in claim 5 wherein the motor and transforming means constitute an elongated assembly, said drilling tool extending at an angle from said assembly.

12. Apparatus as claimed in claim 11 comprising a pivotable cover member coupled to said assembly for movement between a first position in which said tool is covered and a second position in which said tool is exposed.

13. Apparatus as claimed in claim 5 comprising a tubular member surrounding said tool, said tubular member having a free extremity and means supporting the tubular member such that the free extremity extends beyond the tool and can be maintained in contact with the material to be drilled.

14. Apparatus as claimed in claim 13 wherein said means supporting the tubular member comprises an elastic bellows for receiving waste.

15. Apparatus as claimed in claim 5 wherein said motor has an axis of rotation and said driving member is driven in alternating rotation about an axis which is coaxial with the axis of rotation of the motor.

* * * * *